US012734370B2

(12) United States Patent
Wang et al.

(10) Patent No.: US 12,734,370 B2
(45) Date of Patent: Sep. 15, 2026

(54) NANOPATTERNED SOFT-MAGNETIC MATERIAL-BASED MICROCOIL FOR HIGHLY FOCUSED, LOW-POWER, IMPLANTABLE MAGNETIC STIMULATION

(71) Applicant: Regents of the University of Minnesota, Minneapolis, MN (US)

(72) Inventors: Jian-Ping Wang, Minneapolis, MN (US); Renata Saha, Minneapolis, MN (US); Diqing Su, Minneapolis, MN (US); Kai Wu, Minneapolis, MN (US)

(73) Assignee: Regents of the University of Minnesota, Minneapolis, MN (US)

(*) Notice: Subject to any disclaimer, the term of this patent is extended or adjusted under 35 U.S.C. 154(b) by 1018 days.

(21) Appl. No.: 17/995,229

(22) PCT Filed: Apr. 1, 2021

(86) PCT No.: PCT/US2021/025322
§ 371 (c)(1),
(2) Date: Sep. 30, 2022

(87) PCT Pub. No.: WO2021/202840
PCT Pub. Date: Oct. 7, 2021

(65) Prior Publication Data

US 2023/0173293 A1 Jun. 8, 2023

Related U.S. Application Data

(60) Provisional application No. 63/004,851, filed on Apr. 3, 2020.

(51) Int. Cl.

| | |
|---|---|
| ***A61N 2/02*** | (2006.01) |
| ***A61N 1/04*** | (2006.01) |
| ***A61N 2/00*** | (2006.01) |

(52) U.S. Cl.
CPC ................ *A61N 2/02* (2013.01); *A61N 1/04* (2013.01); *A61N 2/002* (2013.01); *A61N 2/006* (2013.01)

(58) Field of Classification Search
CPC ................................................ A61N 2/00–12
See application file for complete search history.

(56) References Cited

U.S. PATENT DOCUMENTS

| | | |
|---|---|---|
| 6,280,376 B1 | 8/2001 | Holcomb |
| 6,678,562 B1 | 1/2004 | Tepper et al. |

(Continued)

FOREIGN PATENT DOCUMENTS

| | | | |
|---|---|---|---|
| CN | 204121602 U | | 1/2015 |
| CN | 103432689 B | * | 2/2016 |

(Continued)

OTHER PUBLICATIONS

Yamaguchi et al., Real-space observation of current-driven domain wall motion in submicron magnetic wires, Physical Review Letters, vol. 92, No. 7, pp. 077205-1-077205-4, 2004.

(Continued)

*Primary Examiner* — Thaddeus B Cox
(74) *Attorney, Agent, or Firm* — Theodore M. Magee; Westman, Champlin & Koehler, P.A.

(57) ABSTRACT

A stimulator includes a support layer, a coil supported by the support layer, the coil extending around a central area, and a plurality of pillars supported by the support layer in the central area.

23 Claims, 13 Drawing Sheets

(56) References Cited

U.S. PATENT DOCUMENTS

| | | | | |
|---|---|---|---|---|
| 9,999,781 | B2 | 6/2018 | Gale et al. | |
| 10,201,715 | B2 | 2/2019 | Wang et al. | |
| 10,213,615 | B2 | 2/2019 | Gale et al. | |
| 2004/0006264 | A1 | 1/2004 | Mojarradi et al. | |
| 2005/0275497 | A1 | 12/2005 | Ramadan et al. | |
| 2006/0212097 | A1 | 9/2006 | Varadan et al. | |
| 2007/0067004 | A1 | 3/2007 | Boveja et al. | |
| 2009/0157151 | A1 | 6/2009 | Cauller et al. | |
| 2009/0248098 | A1 | 10/2009 | Penny et al. | |
| 2010/0324642 | A1 | 12/2010 | Pettinelli | |
| 2012/0078327 | A1 | 3/2012 | Sloan et al. | |
| 2014/0081073 | A1 | 3/2014 | Nishi et al. | |
| 2014/0163305 | A1 | 6/2014 | Watterson | |
| 2016/0303392 | A1 | 10/2016 | Wang et al. | |
| 2017/0001003 | A1 | 1/2017 | Pivonka et al. | |
| 2017/0225004 | A1* | 8/2017 | Casse | A61N 2/02 |
| 2018/0133460 | A1 | 5/2018 | Townley et al. | |
| 2019/0099609 | A1 | 4/2019 | Lee et al. | |
| 2019/0172998 | A1 | 6/2019 | Tan et al. | |
| 2019/0231264 | A1 | 8/2019 | Higbie et al. | |
| 2020/0306539 | A1* | 10/2020 | Kim | A61N 1/3787 |
| 2021/0299656 | A1* | 9/2021 | Malic | B01L 3/502707 |
| 2022/0176141 | A1 | 6/2022 | Caparso et al. | |
| 2022/0362570 | A1 | 11/2022 | Pemberton | |
| 2023/0149729 | A1 | 5/2023 | Wang et al. | |

FOREIGN PATENT DOCUMENTS

| | | | | |
|---|---|---|---|---|
| KR | 102529408 | B1 * | 5/2023 | A61N 1/3787 |
| WO | 2015153868 | A1 | 10/2015 | |
| WO | 2018227165 | A1 | 12/2018 | |
| WO | 2019100055 | A1 | 5/2019 | |
| WO | 2021202834 | A1 | 10/2021 | |
| WO | 2023025939 | A1 | 3/2023 | |
| WO | 2025049951 | A1 | 3/2025 | |

OTHER PUBLICATIONS

Yao et al., Improved current switching symmetry of the magnetic tunneling junction and giant magnetoresistance devices with nano-current-channel structure, Journal of Applied Physics, vol. 115, pp. 07A717-1-07A717-3, 2008.
Yue et al., Magneto-electric nano-particles for non-invasive brain stimulation, Open Access, PLOS One, vol. 7, No. 9, pp. 1-5, 2012.
Zhang et al., High power and low critical current spin torque oscillation from a magnetic tunnel junction with a built-in hard axis polarizer, Applied Physics Letters, vol. 100, pp. 032405-1-032405-4, 2012.
Notification of Transmittal of the International Search Report and the Written Opinion of the International Searching Authority, or the Declaration, International Search Report and Written Opinion dated Jul. 8, 2021 for corresponding International Application No. PCT/US2021/025322, 13 pages.
Notification of Transmittal of the International Search Report and the Written Opinion of the International Searching Authority, or the Declaration, International Search Report and Written Opinion dated Jul. 8, 2021 for corresponding International Application No. PCT/US2021/025313, 11 pages.
Amaral et al., Towards a system to measure action potential on mice brain slice with local magneto resistive probes, Journal of Applied Physics 109, 07B308, 14 pages, 2011.
Banks, Neurotechnology, Engineering Science and Education Journal, pp. 135-144, 1998.
Barach et al., Magnetic Measurements of Action Currents in a Single Nerve Axon: A Core-Conductor Model, IEEE Transactions on Biomedical Engineering, vol. BME-32, No. 2, pp. 136-140, 1985.
Bartorelli et al., Aspirin Alone Antiplatelet Regimen After Intracoronary Placement of the Carbostent, Catheterization and Cardiovascular Interventions, vol. 55, pp. 150-156, 2002.
Berger, Motion of a magnetic domain wall traversed by fast-rising current pulses, Journal of Applied Physics, vol. 71, No. 6, pp. 2721-2726, 1992.
Bhowmik et al., Deterministic domain wall motion orthogonal to current flow due to spin orbit torque, Scientific Reports, 10 pages, 2015.
Bloom et al., 1/f noise reduction of metal-oxide semiconductor transistors by cycling from inversion to accumulation, Applied Physics Letters, vol. 58, No. 15, pp. 1664-1666, 1991.
Bohning, Mapping transcranial magnetic stimulation (TMS) fields in vivo with MRI, Neuro Report, vol. 8, pp. 2535-2538, 1997.
Bonmassar et al., Microscopic magnetic stimulation of neural tissue, Nature Communications, vol. 3, No. 921, Article, 10 pages, 2012.
Burmeister et al., Glutaraldehyde cross-linked glutamate oxidase coated microelectrode arrays: selectivity and resting levels of glutamate in the CNS, ACS Chemical Neuroscience, vol. 4, pp. 721-728, 2013.
Cardoso et al., Magnetic tunnel junction sensors with pTesla sensitivity, Microsystem Technology, 11 pages, 2013.
Chaves et al., MgO based picotesla field sensors, Journal of Applied Physics, vol. 103, pp. 07E931-1-07E931-3, 2008.
Chen et al., Direct electrochemical oxidation of NADPH at a low potential on the carbon nanotube modified glassy carbon electrode, Chinese Journal of Chemistry, vol. 22, No. 2, pp. 167-171, 2004.
Chen et al., Wireless magnetothermal deep brain stimulation, Research, Neurotechniques, vol. 347, No. 6229, pp. 1477-1480, 2015.
Cheung, Implantable microscale neural interfaes, Biomed Microdevices, vol. 9, pp. 923-938, 2007.
Clark et al., A mathematical evaluation of the core conductor model, Biophysical Journal, vol. 6, pp. 95-112, 1966.
Cogan, Neural stimulation and recording electrodes, Annual Review of Biomedical Engineering, vol. 10, pp. 275-309, 2008.
Cogan et al., Sputtered iridium oxide films (SIROFs) for low-impedance neural stimulation and recording electrodes, Proceedings of the 26th Annual International Conference on the IEEE EMBS, pp. 4153-4156, 2004.
Cohen, Magnetoencephalography: Evidence of Magnetic Fields Produced by Alpha-Rhythm Currents, Science, vol. 161, pp. 784-786, 1968.
Dey et al., Nanomaterial-based functional scaffolds for amperometric sensing of bioanalytes, Anal Bioanal Chemical, vol. 405, pp. 3431-3448, 2013.
Dhanapal et al., Reversibly controlled magnetic domains of Co film via electric field driven oxygen migration at nanoscale, Applied Physics Letter, vol. 114, No. 23, 7 pages, 2019.
Di et al., Influence of controlled surface oxidation on the magnetic anisotropy of Co ultrathin films, Applied Physics Letter, vol. 106, 5 pages, 2015.
Dichter, Rat cortical neurons in cell cultrue: culture methods, cell morphology, electrophysiology, and synapse formation, Brain Research, vol. 149, pp. 279-293, 1978.
Dierickx et al., The decrease of "random telegraph signal" noise in metal-oxide semiconductor field-effect transistors when cycled from inversion to accumulation, Journal of Applied Physics, vol. 71, No. 4, pp. 2028-2029, 1993.
Duan et al., Tauroursodeoxycholic acide improves the survival and function of nigral transplants in a rat model of Parkinson's disease, Cell Transplantation, vol. 11, pp. 195-205, 2002.
Enz et al., Circuit techniques for reducing the effects of op-amp imperfections: autozero, correlated double sampling, and chopper stabilization, Proceedings of the IEEE, vol. 84, No. 11, pp. 1584-1614, 1996.
Fukami et al., Current-induced domain wall motion in perpendicularly magnetized coFeB nanowire, Applied Physics Letters, vol. 98, pp. 082504-1-082504-3, 2011.
Golestanirad et al., Solenoidal micromagnetic stimulation enables activation of axons with specific orientation, Frontiers in Physiology, Technology Report, vol. 9, Article 724, 15 pages, 2018.
Grill-Spector et al., Differential processing of objects under various viewing conditions in the human lateral occipital complex, Neuron, vol. 24, pp. 187-203, 1999.

(56) References Cited

OTHER PUBLICATIONS

HajjHassan et al., NeuroMEMS: Neural probe microtechnologies, Sensors, vol. 8, pp. 6704-6726, 2008.
Hamalainen et al., Magnetoencephalography-theory, instrumentation, and applications to noninvasive studies of the working human brain, Reviews of Modern Physics, vol. 65, No. 2, 93 pages, 1993.
Hascup et al., Microelectrode array fabrication and optimization for selection neurochemical detection, Microelectrode Biosensors, Meuromethods, vol. 80, pp. 27-54, 2013.
Hu et al., Opportunities and challenges for magnetoelectric devices, Applied Physics Letters, vol. 7, pp. 080905-1-080905-16, 2019.
Intechopen, http://www.intechopen.com, 1 page, accessed 2016.
Jang et al., Two distinct filopodia populations at the growth cone allow to sense nanotopographical extracellular matrix cues to guide neurite outgrowth, Open Access, Sensing of ECM Nanotopographical Cues by Filopodia, vol. 5, No. 12, 11 pages, 2010.
Jansen et al., Transplantation of fetal neocortex ameliorates sensorimotor and locomotor deficits following neonatal schemic-hypoxic brain injury in rats, Experimental Neurology, vol. 147, pp. 487-497, 1997.
Kassim et al., Tail current flicker noise reduction in LC VCOs by complementary switched biasing, ICM, pp. 102-105, 2003.
Kegley, Testing the efficiency of vertically aligned gold nanowires on a titanium needle implantable neural electrodes in the Rattus Norvegicus Hipposcampus, University of Arkansas, ScholarWorks@UARK, Electrical Engineering Undergraduate Honors, Theses, 41 pages, 2012.
Kim et al., Electroanalytical eavesdropping on single cell communication, Analytical Chemistry, vol. 83, pp. 7242-7249, 2011.
Kim et al., A low-noise WLAN mixer using switched biasing technique, IEEE Microwave and Wireless Components Letters, vol. 19, No. 10, pp. 650-652, 2009.
Kohlmeier et al., An investigation on technologies to fabricate microcoils for miniaturized actuator systems, Microsystem Technologies, vol. 10, pp. 175-181, 2004.
Lee et al., Polyimide-based intracortical neural implant with improved structural stiffness, Journal of Micromechanics and Microengineering, vol. 14, pp. 32-37, 2004.
Lee et al., Wheatstone bridge giant-magnetoresistance based cell counter, Biosensors and Bioelectronics, vol. 57, pp. 48-53, 2014.
Lee et al., Implantable microcoils for intracortical magnetic stimulation, Science Advances, Research Article, Bioengineering, vol. 2, 14 pages, 2016.
Lind et al., The density difference between tissue and neural probes is a key factor for glial scarring, Scientific Reports, vol. 3, 7 pages, 2013.
Liou, High sensitivity magnetoresistive sensors for both DC and EMI magnetic field mapping, University of Nebraska, SERDP Project MR-1716, 19 pages, 2012.
Lorach et al., Neural stimulation for visual rehabilitation: advances and challenges, Journal of Physiology, pp. 421-431, 2013.
Love et al., Diamond like carbon coatings for potential application in biological implants—a review, Tribology International, vol. 63, pp. 141-150, 2013.
Lyle et al., Direct communication between magnetic tunnel junctions for nonvolatile logic fan-out architecture, Applied Physics Letters, vol. 97, pp. 152504-1-152504-3, 2010.
Malmivuo, Comparison of the properties of EEG and MEG in detecting the electric activity of the brain, Brain Topogr, vol. 25, pp. 1-19, 2012.
Malmivuo, Bioelectromagnetism: Principles and Applications of Bioelectric and BioMagnetic Fields, Oxford University Press, Part 1, pp. 1-129, 1995.
Malmivuo, Bioelectromagnetism: Principles and Applications of Bioelectric and BioMagnetic Fields, Oxford University Press, Part 2, pp. 130-257, 1995.
Malmivuo, Bioelectromagnetism: Principles and Applications of Bioelectric and BioMagnetic Fields, Oxford University Press, Part 3, pp. 258-385, 1995.
Malmivuo, Bioelectromagnetism: Principles and Applications of Bioelectric and BioMagnetic Fields, Oxford University Press, Part 4, pp. 386-513, 1995.
Malmivuo, Bioelectromagnetism: Principles and Applications of Bioelectric and BioMagnetic Fields, Oxford University Press, Part 5, pp. 514-641, 1995.
Maynard et al., The Utah intracortical electrode array: a recording structure for potential brain-computer interfaces, Electroencephalography and Clinical Neurophysiology, vol. 102, pp. 228-239, 1997.
Medtronic, http://www.medtronic.com/innovation/smarter-dbs.html#sthash.D7onn0eo.dpuf, accessed 2016.
Metz et al., Flexible polyimide probes with microelectrodes and embedded microfluidic channels for simultaneous drug delivery and multi-channel monitoring of bioelectric activity, Biosensors and Bioelectronics, vol. 19, pp. 1309-1318, 2004.
Minusa et al., A multichannel magnetic stimulation system using submillimeter-sized coils: system developed and experimental application to rodent brain in vivo, Journal of Neural Engineering, vol. 16, 21 pages, 2019.
Normann et al., A neural interface for a cortical vision prosthesis, Vision Research, vol. 39, pp. 2577-2587, 1999.
Ordonez e al., Improved polyimide thin-film electrodes for neural implants, 34th Annual International Conference of the IEEE, pp. 5134-5137, 2012.
Park et al., Activation of the central nervous system induced by micro-magnetic stimulation, Nature Communications, 9 pages, 2013.
Parkin et al., Magnetic domain-wall racetrack memory, Science, vol. 320, pp. 190-194, 2008.
Parkinson, http://www.parkinson.org, accessed 2016.
Pearce et al., Microtechnology, Meet neurobiology, Critical Review, The Royal Society of Chemistry, Lab Chip, vol. 7, pp. 30-40, 2007.
Pong et al., Hysteresis loop collapse for linear response in magnetic-tunnel-junction sensors, Journal of Applied Physics, vol. 105, pp. 07E723-1-07E723-3, 2009.
Pundt et al., Transplantation of human striatal tissue into a rodent model of Huntington's Disease: phenotypic expression of transplanted neurons and host-to-graft innervation, Brain Research Bulletin, vol. 39, No. 1, pp. 23-32, 1996.
Rahman et al., Reduction of switching current density in perpendicular magnetic tunnel junctions by tuning the anisotropy of the CoFeB free layer, Journal of Applied Physics, vol. 11, pp. 07C907-1-07C907-3, 2012.
Ramadan et al., Fabrication of three-dimensional magnetic microdevices with embedded microcoils for magnetic potential concentration, Journal of Microelectromechanical Systems, vol. 15, No. 3, pp. 624-638, 2006.
Reinhoud et al., Analysis of glutamate, GABA, noradrenaline, dopamine, serotonin, and metabolites using microbore UHPLC with electrochemical detection, ACS Chemical Neuroscience, vol. 4, pp. 88-894, 2013.
Riklin et al., Glucose and acetylcholine sensing multilayer enzyme electrodes of controlled enzyme layer thickness, Anal. Chem., vol. 67, pp. 4118-4126, 1995.
Rizou et al., Magnetic stimulation in the microscale: the development of a 6×6 array of microcoils for stimulation of excitable cells in vitro, Biomedical Physics & Engineering Express, 14 pages, 2017.
Romani, Fundamentals of Neuromagnetism, Advances in Biomagnetisum, pp. 33-46, 1989.
Roth et al., The magnetic field of a single axon, Journal of Biophysical Society, vol. 48, pp. 93-109, 1985.
Rousche et al., Flexible polyimide-based intracortical electrode arrays with bioactive capability, IEEE Transactions on Biomedical Engineering, vol. 48, No. 3, pp. 361-371, 2001.
Roy et al., Biomedical applications of diamond-like carbon coatings: a review, Wiley, Interscience, pp. 72-84, 2006.
Rubehn et al., A MEMS-based flexible multichannel ECoG-electrode array, Journal of Neural Engineering, vol. 6, 10 pages, 2009.
Saha, Tunable magnetic skyrmions in spintronic nanostructures for cellular-level magnetic neurostimulation, Journal of Physics D: Applied Physics, vol. 52, 11 pages, 2019.

(56) References Cited

OTHER PUBLICATIONS

Saltzberg et al., Pharmacological characterization of P2Y receptor subtypes on isolated tiger salamander muller cells, GLIA, vol. 42, pp. 149-159, 2003.
Shinwari et al., Microfabricated reference electrodes and their biosensing applications, Sensors, vol. 10, pp. 1679-1715, 2010.
Srinivasan et al., A detection system based on giant magnetoresistive sensors and high-moment magnetic nanoparticles demonstrates zeptomole sensitivity: potential for personalized medicine, Communications, Biosensors, Angew, Chem. Int. Ed., vol. 48, pp. 2764-2767, 2009.
Su et al., Tunable magnetic domain walls for therapeutic neuromodulation at cellular level: stimulating neurons through magnetic nanowires, Journal of Applied Physics, vol. 126, 14, pages, 2019.
Suh et al., Neurovascular coupling and oximetry during epileptic events, Molecular Neurobiology, vol. 33, pp. 181-197, 2006.
Tan et al., Magneto-ionic control of magnetisum using a solid-state proton pump, Nature Materials, vol. 18, pp. 35-42, 2019.
Tanghe et al., A 16-channel CMOS neural stimulating array, IEEE Journal of Solid-State Circuits, vol. 27, No. 12, pp. 1819-1825, 1992.
Tetienne et al., Nitrogen-vacancy-center imaging of bubble domains in a 6-A film of cobalt with perpendicular magnetization, Journal of Applied Physics, vol. 115, pp. 17D501-1-17D501-3, 2014.
Triarhou et al., Transplantation of ventral mesencephalic analgen to a genetic model of nigrostriatal dopamine deficiency, Proceedings of the National Academy of Science, vol. 83, pp. 8789-8793, 1986.
Van der Wel, MOSFET 1/f noise measurement under switched bias condictidons, IEEE Electron Device Letters, vol. 21, No. 1, pp. 43-46, 2000.
Viventi et al., Flexible foldable actively multiplexed, high-density electrode array for mapping brain activity in vivo, Nature Neuroscience, Technical Reports, vol. 14, No. 12, pp. 1599-1607, 2011.
Weiland et al., In vitro electrical properties for iridium oxide versus titanium nitride stimulating electrodes, IEEE Transactions on Biomedical Engineering, vol. 49, No. 12, pp. 1574-1579, 2022.
West et al., A simple model for calculating magnetic nano-wire domain wall fringing fields, Journal of Physics D: Applied Physics, vol. 45, pp. 1-9, 2012.
Wikipedia, https://en.wikipedia.org/wiki/neurostimulation, 2016.
Winkin et al., Flexible multi-electrode array with integrated bendable CMOS-chip for implantable systems, 34th Annual International Conference of the IEEE EMBS, pp. 3882-3885, 2012.
Wise et al., Microfabrication techniques for integrated sensors and microsystems, Science, pp. 1335-1342, 1991.
Wise et al., An integrated-circuit approach to extracellular microelectrodes, IEEE Transactions on Bio-Medical Engineering, vol. BME-17, No. 2, pp. 238-247, 1970.
Wise et al., Wireless implantable microsystems: high-density electronic interfaces to the nervous system, Proceedings of the IEEE, vol. 92, No. 1, pp. 76-97, 2004.
Woosley et al., The magnetic field of a single axon: a volume conductor model, Mathematical Biosciences, vol. 76, pp. 1-36, 1985.
Wu et al., Spin-oribt torque and spin hall effect-based cellular level therapeutic spintronic neuromodulator: a simulation study, The Journal of Physical Chemistry, vol. 123, pp. 24963-24972, 2019.
Prosecution history of U.S. Appl. No. 17/995,237 including: Final Office Action dated Feb. 24, 2026, Amendment dated Dec. 23, 2025, Office Action dated Sep. 24, 2025, 91 pages.
PCT Notification of Transmittal of the International Search Report and the Written Opinion of the International Searching Authority, or the Declaration dated Jan. 15, 2025 for corresponding PCT application Serial No. PCT/US2024/044736, 12 pages.
Angotzi et al., A programmable closed-loop recording and stimulating wireless system for behaving small laboratory animals, Scientific Reports, 4:5963, 2014.
Bloom et al., Portable Arbitrary Pulse Generator for Driving μCoils for Micromagnetic Neurostimulation, bioRxiv preprint doi: https://doi.org./10.1101/2023.06.19.545512, 14 pages, 2026.
Chappert et al., The emergence of spin electronics in data storage, Nature Mater 6, https://doi.org/10.1038/nmat2024, 813-823, 2007.
Ho et al., Wireless power transfer to deep-tissue microimplants, PNAS, vol. 11, No. 22, pp. 7974-7979, 2014.
Rolston et al., A low-cost multielectrode system for data acquisition enabling real-time closed-loop processing with rapid recovery from stimulation artifacts, Frontiers in Neuroengineering, Original Research Article, vol. 2, Article 12, 17 pages, 2009.
Saha et al., Impact of anesthesia on micromagnetic stimulation (μMS) of the vagus nerve, Biomedical Physics & Engineering Express, vol. 10, 11 pages, 2024.
Saha et al., Micromagnetic stimulation (μMS) dose-response of the rat sciatic nerve, Journal of Neural Engineering, vol. 20, 16 pages, 2023.
Saha et al., Micromagnetic stimulation (μMS) controls dopamine release: an in vivo study using WINCS Harmoni, Biomedical Physics & Engineering Express, vol. 11, 14 pages, 2025.
Tonini et al., Feasibility study of magnetic sensing for detecting single-neuron action potentials, Annals of Biomedical Science and Engineering, pp. 19-29, 2022.
Wu et al., Giant magnetoresistance biosensors in biomedical applications, ACS Appl Mater Interfaces, 49 pages, 2022.
https://www.youtube.com/watch?v=Wiy_eHdj8kg, 7 pages, retrieve as early as 2026.

* cited by examiner 620
630
102
138
140
110
172
128
124
170
122
126
174
164
160
150
158
105
162
171
176
106
107
168
104
180
178
166

NANOPATTERNED SOFT-MAGNETIC MATERIAL-BASED MICROCOIL FOR HIGHLY FOCUSED, LOW-POWER, IMPLANTABLE MAGNETIC STIMULATION

CROSS-REFERENCE OF RELATED APPLICATION

This application is a Section 371 National Stage Application of International Application No. PCT/US2021/025322, filed Apr. 1, 2021, which is incorporated by reference in its entirety and published as WO 2021/202840A1 on Oct. 7, 2021 and which claims priority of U.S. Provisional Application No. 63/004,851, filed Apr. 3, 2020.

BACKGROUND

By applying a voltage or a changing magnetic field to a nerve cell, it is possible to cause the nerve cell to "fire" during which the nerve cell depolarizes and then repolarizes.

In external magnetic stimulation, a strong alternating magnetic field is generated external to the body and is directed into the body. Within the body, the time-varying magnetic field induces an electric field that creates a current along the nerve cells which causes them to fire.

Such external systems require strong magnetic fields in order to penetrate into the body. However, as the magnetic fields increase in strength, the area affected by the magnetic fields also increases resulting in low resolution stimulus of the nerve cells. As a result, it is difficult to direct the external magnetic field to only a select number of nerve cells.

In implantable magnetic stimulation, a probe is placed in the vicinity the nerve cells within the body and a magnetic field is generated at the end of the probe to stimulate the nerve so that it fires.

The discussion above is merely provided for general background information and is not intended to be used as an aid in determining the scope of the claimed subject matter. The claimed subject matter is not limited to implementations that solve any or all disadvantages noted in the background.

SUMMARY

A stimulator includes a support layer, a coil supported by the support layer, the coil extending around a central area, and a plurality of pillars supported by the support layer in the central area.

A method of medical treatment includes placing a magnetic field generator near target tissue. The magnetic field generator includes a conductive coil that wraps around a central volume and a plurality of pillars located in the central volume. A series of current pulses is applied to the conductive coil so as to generate a magnetic field that passes through the pillars and interacts with the target tissue.

In accordance with a further embodiment, a medical treatment device includes a plurality of magnetic pillars and a coil wrapping around the plurality of medical pillars. A controller is configured to apply a current to the coil to create a magnetic field that passes through the magnetic pillars.

In accordance with some embodiments the coil is made of gold and the pillars are made of a permalloy. In accordance with one embodiment each pillar and the coil have a same height above the support layer. In accordance with another embodiment, each pillar has a height above the support layer that is greater than a height of the coil above the support layer.

In accordance with one embodiment, the plurality of pillars is an array of pillars with rows and columns.

In accordance with one embodiment, the stimulator further includes an additional plurality of pillars located between turns of the coil. In accordance with one such embodiment, the additional plurality of pillars located between turns of the coil have a lower magnetic flux density than the plurality of pillars in the central area.

In accordance with one embodiment, the stimulator further includes an insulating layer over the coil and the plurality of pillars.

In accordance with one embodiment, each of the pillars has a linear change in the magnetic field generated by the pillar for an applied magnetic field.

In accordance with some embodiments, the magnetic field interacts with the tissue to stimulate at least one neuron. In accordance with other embodiments, the magnetic field interacts with the tissue to destroy the tissue.

In accordance with some embodiments, the coil has an outer perimeter that is less than 300 micrometers and each of the plurality of magnetic pillars has a height that is less than 25 micrometers.

In accordance with the various embodiments, the magnetic pillars comprise one or more of a FeSiAl alloy, a FeSi alloy, a Fe—N alloy such as Minnealloy ($Fe_{16}CN$) and a magnetic soft nanocrystalline material. In accordance with embodiments in which a pillar is a magnetic soft nanocrystalline material, the pillar material is one of a group consisting of FeCuNbSiB and CoZrNb.

In accordance with one embodiment, in the stimulator and medical treatment device 30, at least one of the magnetic pillars functions as an electrode to enable both magnetic and electric stimulation simultaneously.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DETAILED DESCRIPTION

Embodiments described below provide a magnetic field generator that consists of a coil surrounding a plurality of pillars of magnetic material. A series of current pulses are applied to the coil to create a magnetic field with a changing flux density. As the current increases, the flux density increases and as the current decreases, the flux density decreases. When applied to neurons, these changes in the flux density can create a current in neurons that causes the neurons to fire. When applied to other tissue at high enough frequencies, the changing flux density can kill the cells of the tissue.

By using a plurality of pillars in the center of the coil instead of a single large core, the embodiments concentrate the magnetic flux by providing less surface area for the magnetic flux to pass through. If a single smaller pillar was used, there would be an increased chance that the pillar would not be aligned with the target neuron or cell cluster. By providing a plurality of spaced pillars, the surface area is reduced while still making it likely that the target neuron or cells will align with at least one pillar.

The magnetic field generator may be implemented on the end of a probe that is inserted into the body, on an external device that applies the magnetic field to the exterior of the body or in an implantable device that is placed within a patient.

Figure 1:
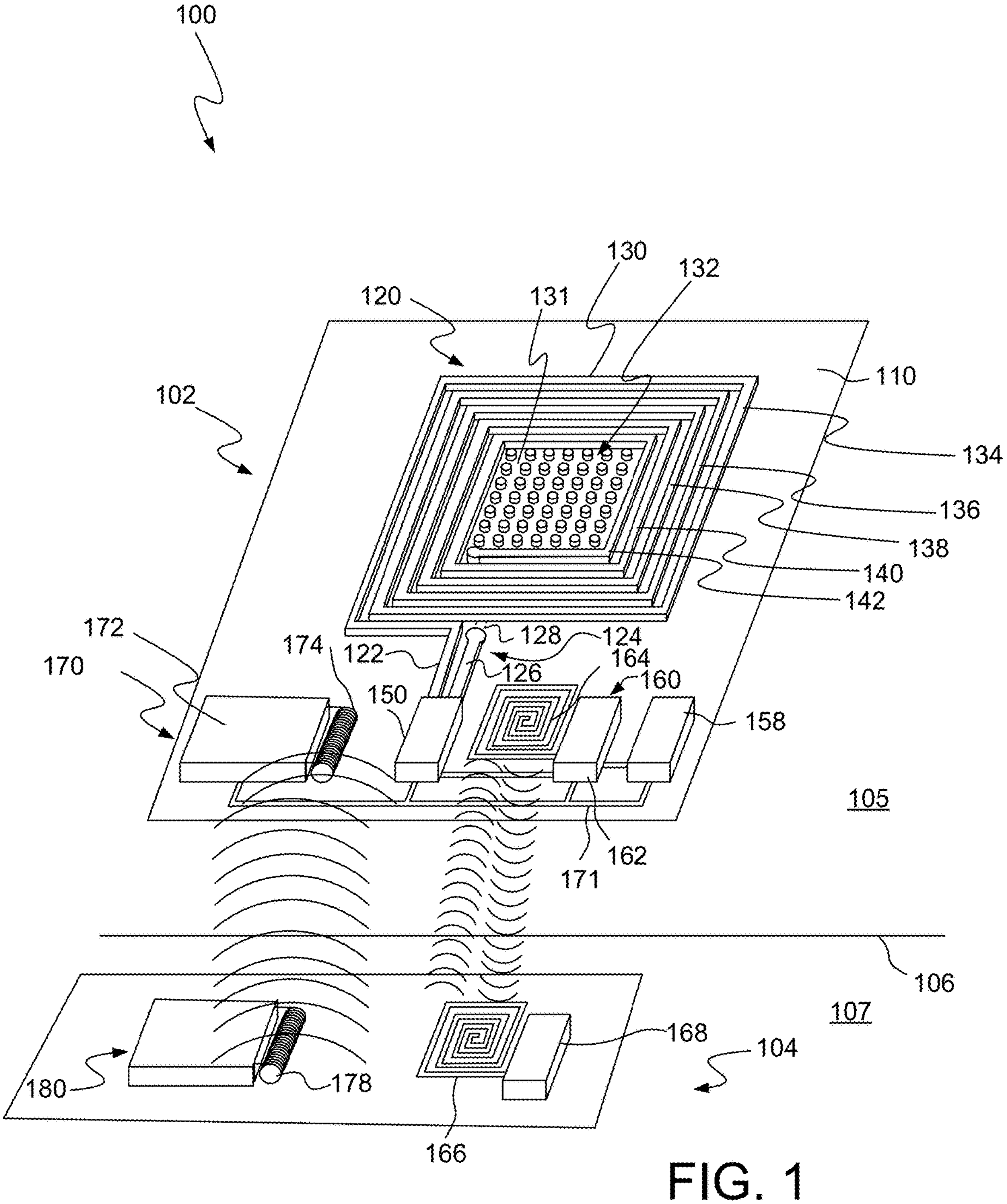
FIG. 1 is a schematic diagram of a system for providing magnetic field treatments in accordance with one embodiment.

FIG. 1 provides a schematic diagram of a system 100 that provides an implantable embodiment of the magnetic field generator. System 100 includes an implanted device 102 and an external device 104. Implanted device 102 is located within a living body 105 and external device 104 is located in an environment 107 exterior to living body 105 and separated from living body 105 by an outer surface 106 of the living body. In accordance with one embodiment, implanted device 102 is inserted into living body 105 through an incision in outer surface 106 and then the incision is sealed such that there is no wired connection between implanted device 102 and external device 104.

Implanted device 102 includes a flexible support layer 110 having a magnetic field generator or stimulator 120, which generates a fluctuating magnetic field when active that interacts with biological material. Although these interactions can include interfering with the normal operation of the biological material, changing the physical structure of the biological material, changing the operation of the biological material and stimulating the biological material to generate a response from the biological material, for example, the interactions are referred to generically as stimulating the biological materials and implanted device 102 used to generate the fluctuating magnetic field is referred to generically as a stimulator 102 or medical device 102. In the descriptions herein, the reference to stimulating should be read to include all interactions between the magnetic field generating devices and the biological tissue and the references to stimulators should be read to include all devices of the disclosed design that generate a fluctuating magnetic field that interacts with biological tissue.

Figure 2:
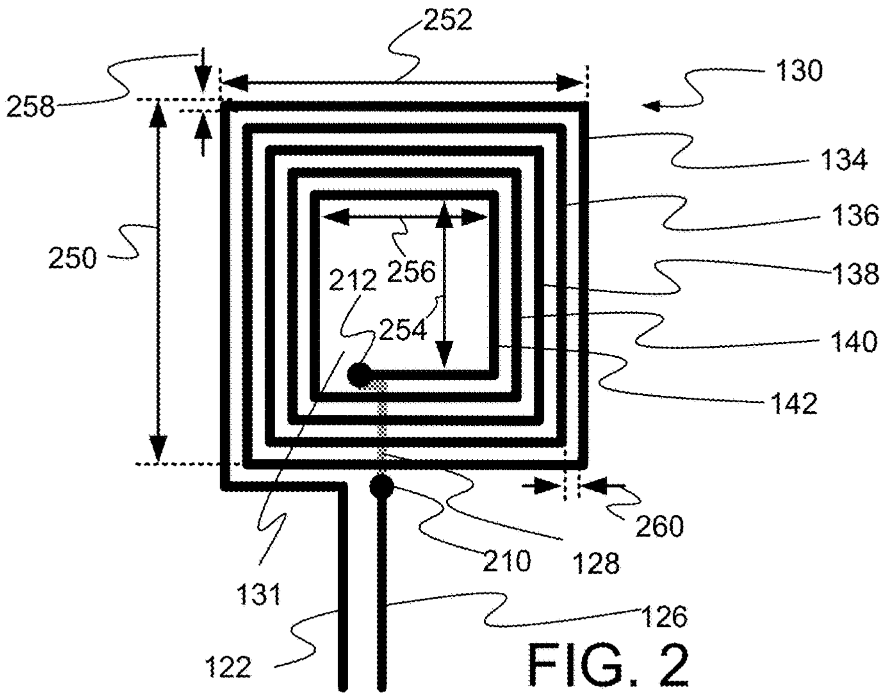
FIG. 2 is a top view of a coil in accordance with one embodiment.

In addition to magnetic field generator 120, a stimulator controller 150, a memory 158, a communication circuit 160 and a power circuit 170 are mounted on flexible support layer 110. Magnetic field generator 120 is connected to stimulator controller 150 by connect lines 122 and 124. Connect line 124 is constructed of a top layer portion 126 and a bottom layer portion 128 (shown in dotted lines) that are connected by vias 210 and 212 (FIG. 2). Magnetic field generator 120 is controlled by applying current to connect lines 122 and 124. In accordance with one embodiment, stimulator controller 150 applies a series of current pulses on connect lines 122 and 124 that cause coil 130 to generate a fluctuating magnetic field that passes through pillars 132. In one particular embodiment, stimulator controller 150 includes a function generator and an amplifier that together form bursts of 2 kHz sine waves having a voltage range of 1-5 volts with a one second interval between bursts.

Communication circuit 160 consists of a wireless communication controller 162 and an antenna 164. Wireless communication controller 162 communicates through antenna 164 to an antenna 166 that is coupled to a wireless communication circuit 168 of external device 104. Through this communication, stimulator controller 150 may receive instructions to stimulate tissue at particular frequencies, intensities and durations. In particular, instructions may pass through wireless communication circuit 168 and antenna 166 and be received by antenna 164 and wireless communication controller 162 before being provided to stimulator controller 150.

Although communication circuit 160 is shown to be wireless in FIG. 1, in other embodiments, a wired connection is provided between implanted device 102 and external device 104.

Power circuit 170 provides power to stimulator controller 150, communication circuit 160 and memory 158 through a power bus 171. Some of the power provided to stimulator controller 150 is routed to magnetic field generator 120 to generate the fluctuating magnetic field.

In accordance with one embodiment, power circuit 170 includes an induction loop 174 that generates an electrical current when it receives an alternating magnetic field 176. The current from induction loop 174 can be used to provide power to power bus 171 directly or can be used to recharge a battery 172 that in turn provides power to power bus 171. In accordance with one embodiment, the alternating magnetic field 176 received by induction loop 174 is generated by a corresponding induction loop 178 in a power system 180 of external device 104. Thus, external device 104 provides power wirelessly to implanted device 102. This power can be provided periodically to charge battery 172 or can be provided continuously to directly power the components of implanted device 102. After battery 172 has been charged, external device 104 can be removed and does not need to be present in order for implanted device 102 to operate since battery 172 can provide power while external device 104 is not present. In accordance with other embodiments, a wired connection between implanted device 102 and external device 104 allows power to be conveyed between external device 104 and implanted device 102 either periodically to recharge battery 172 or continuously to power implanted device 102.

Magnetic field generator 120 includes a coil 130 formed around an inner/central area/volume 131 containing a plurality of pillars 132. In accordance with the embodiment of FIG. 1, coil 130 has five turns 134, 136, 138, 140 and 142. In other embodiments, other numbers of coils are present. In accordance with one embodiment, coil 130 is formed of a non-toxic conductor such as gold. The plurality of pillars 132 includes substantially identical pillars of magnetic material that are spaced apart from each other. In accordance with one embodiment, each pillar of pillars 132 is made of a soft magnetic material, such as permalloy or iron that requires extremely small magnetic field strengths to reach saturation magnetization. In other words, the magnetization of these pillars changes linearly with the magnetic field generated by coil 130 instead of following a hysteresis loop. In the embodiment of FIG. 1, the pillars are arranged in a rectangular array having columns and rows. In other embodiments, the pillars are arranged in other patterns. Additionally, the outer perimeter of the plurality of pillars has other shapes, such as circular, in other embodiments. Coil 130 and pillars 132 are supported by a same level of flexible substrate 110 and have a same height in one embodiment.

FIG. 2 provides a top view of coil 130 in accordance with one embodiment. Coil 130 has a length 250 and a width 252, which in accordance with one embodiment are each less than 300 micrometers, such as 50 micrometers. Inner area 131 has a length 254 and a width 256, which in accordance with one embodiment are both 30 micrometers. Each trace of coil 130 has a width 258, which in accordance with one embodiment is 2 micrometers and each turn of coil 130 is separated from neighboring turns by a space having a width 260, which in accordance with one embodiment is 2 micrometers. Each trace of coil 130 has a height of less than 5 micrometers, such as 2 micrometers in accordance with one embodiment.

Figure 3:
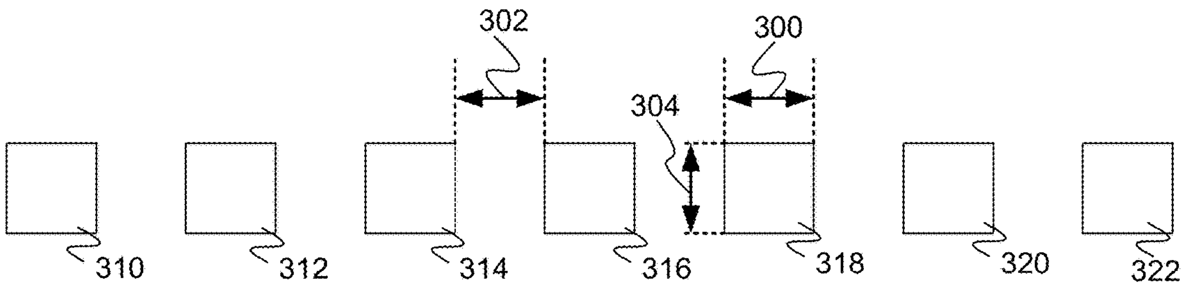
FIG. 3 is a side view of a plurality of pillars in accordance with one embodiment.
Figure 4:
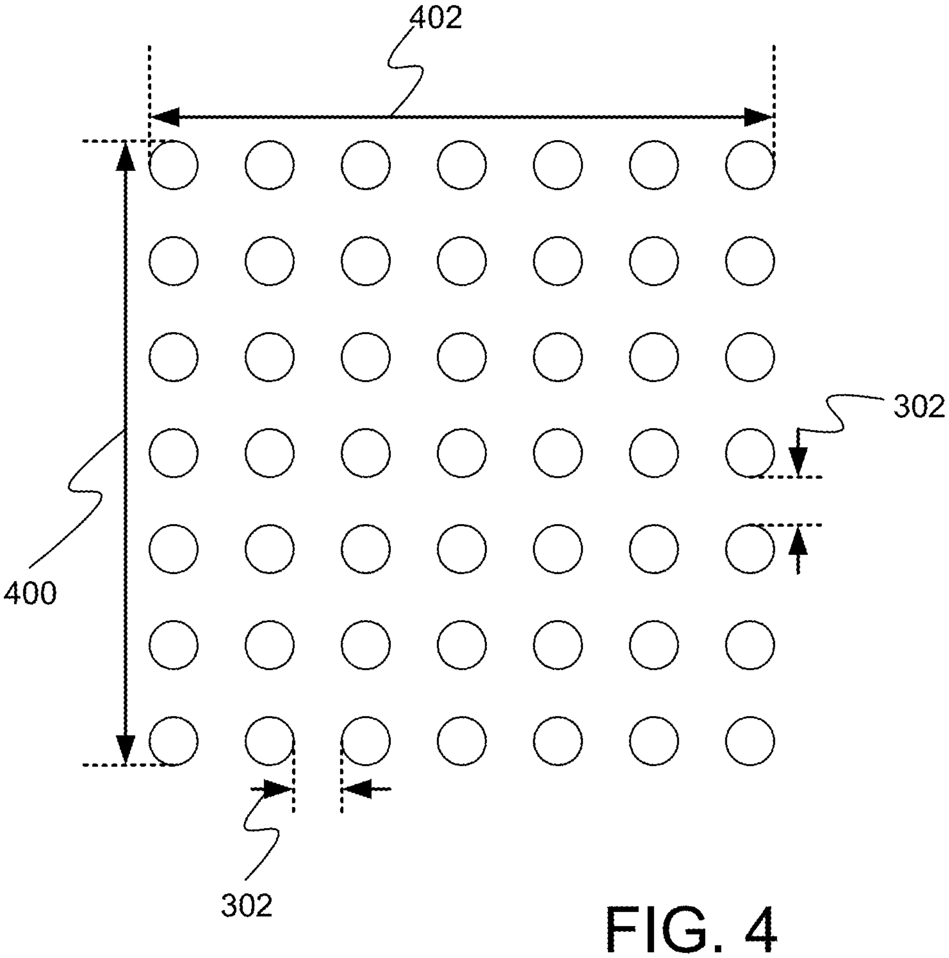
FIG. 4 is a top view of the plurality of pillars of FIG. 3.

FIGS. 3 and 4 provide a side view and a top view, respectively of the plurality of pillars 132 of FIG. 1. Each pillar, such as pillars 310, 312, 314, 316, 318, 320, and 322, have a height 304 and a diameter 300, which in one embodiment are both 2 micrometers. Each pillar is separated from its closest neighboring pillars by a distance 302, which in one embodiment is 2 micrometers. As shown in FIG. 4, the plurality of pillars have a rectangular perimeter with a width 400 and a length 402, which in one embodiment are both 26 micrometers.

Figure 5:
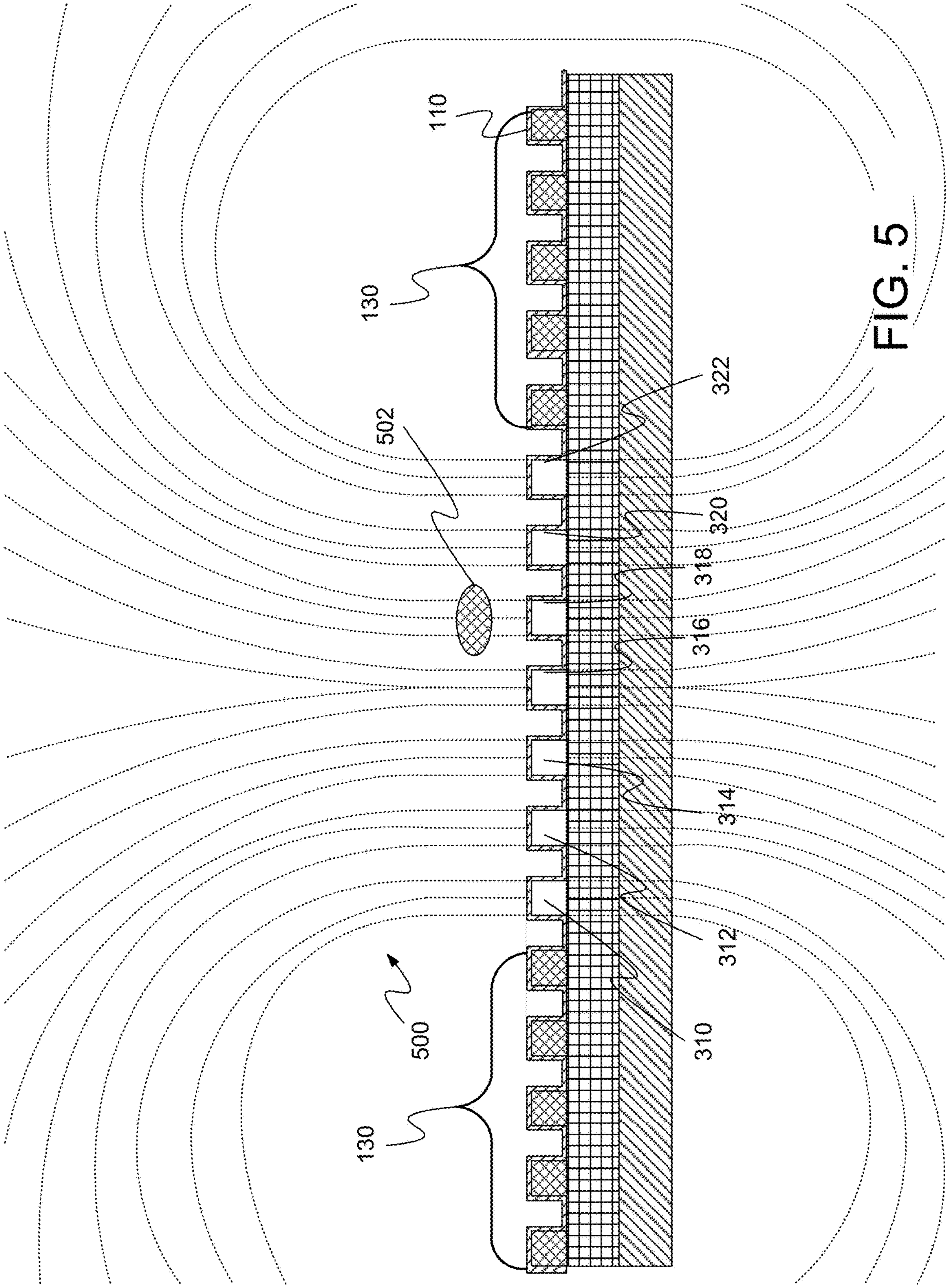
FIG. 5 is a side sectional view of the magnetic field generator of FIG. 1 showing magnetic flux lines.

FIG. 5 provides a side sectional view of magnetic field generator 120 of FIG. 1 showing magnetic flux lines 500 extending from pillars 310, 312, 314, 316, 318, 320 and 322 due to a current in coil 130. As shown in FIG. 5, the magnetic flux is concentrated on the pillars and does not pass through the spaces between the pillars. This increases the magnetic flux density above the pillars. The magnetic flux density produced by coil 130 is further amplified by the magnetism of the pillars. This increase in the magnetic flux density makes it more likely that the magnetic field generated by magnetic field generator 120 will affect tissue such as neuron 502 shown in FIG. 5. In addition, the large number of pillars makes it more likely that the target tissue will be aligned with a pillar and as such will be in the densest part of the magnetic flux.

FIG. 5 also shows a flexible support layer 110 that covers coil 130 and the plurality of pillars 132 and supports coil 130 and pillars 132. Support layer 110 protects coil 130 from shorting when implanted device 102 is placed in contact with human tissue and can be sterilized before implanted device 102 is implanted. In accordance with one embodiment, support layer 110 is parylene C.

Figure 6:
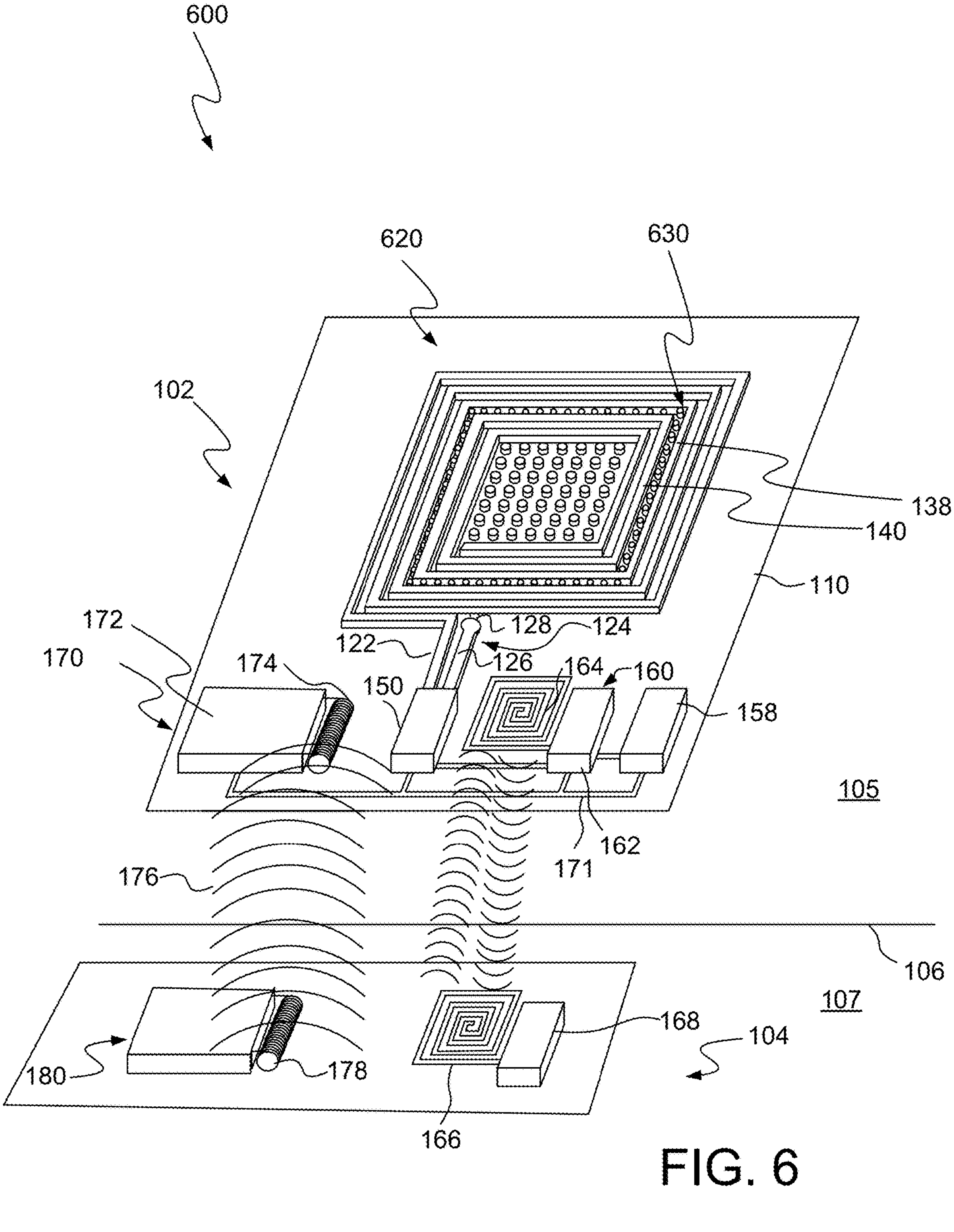
FIG. 6 is a schematic view of a system for providing magnetic field treatments in accordance with a second embodiment.

FIG. 6 provides a schematic view of a system 600 that is identical to system 100 except that the magnetic field generator 620 of FIG. 6 includes pillars 630 between turns 138 and 140 of coil 130. In accordance with one embodiment, pillars 630 have the same height as pillars 132 but have a smaller diameter to fit between turns 138 and 140. Although pillars 630 are shown between turns 138 and 140, these pillars are between other turns in other embodiments and in still further embodiments are between each of the turns of coil 130. The pillars of pillars 630 are spaced apart from each other so as to concentrate the magnetic flux at the pillars.

Figure 7:
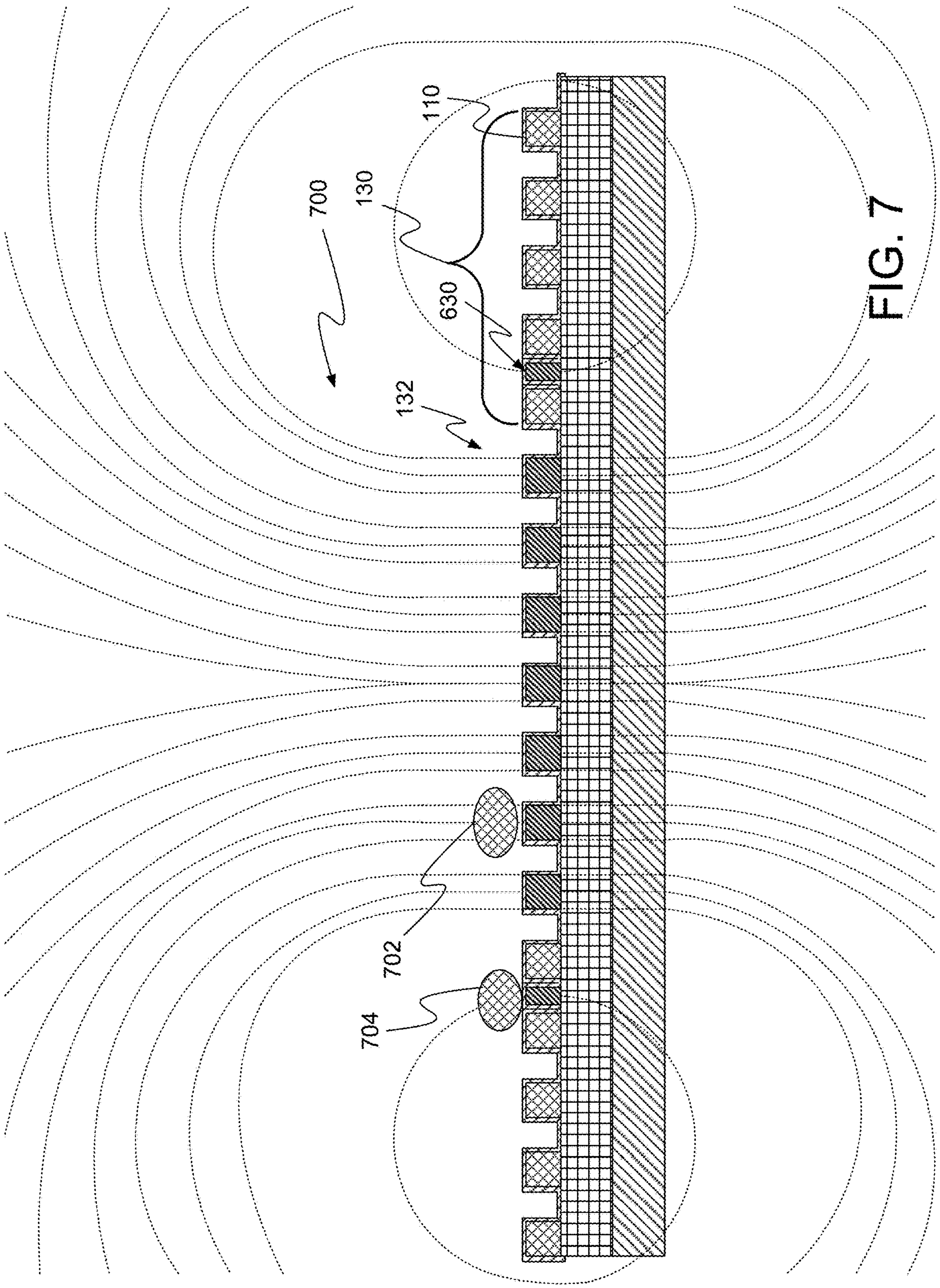
FIG. 7 is a side sectional view of the magnetic field generator of FIG. 6 showing magnetic flux lines.

FIG. 7 shows a side sectional view of magnetic field generator 620 showing magnetic flux lines 700. As shown in FIG. 7, the magnetic flux density in pillars 630 is less than the magnetic flux density in pillars 132 due to the fact that pillars 630 are surrounded by fewer turns of coil 130. By providing pillars with different magnetic flux density, it is possible to apply different field strengths to different target cells. For instance, in FIG. 7, cell 702 receives a greater magnetic flux density than cell 704.

Figure 8:
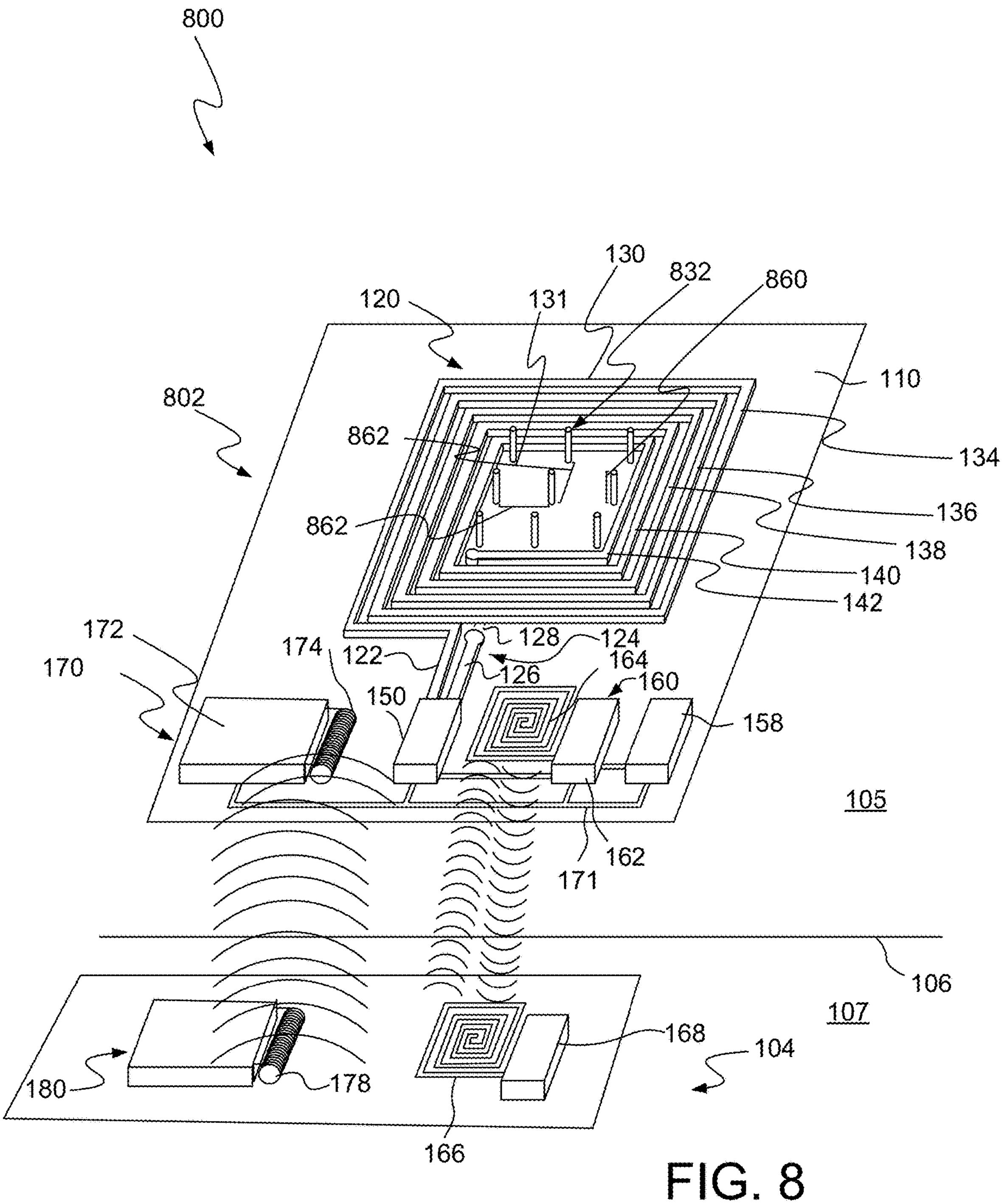
FIG. 8 is a schematic view of a system for providing magnetic field treatments in accordance with a third embodiment.

FIG. 8 provides a schematic view of a system 800 that is identical to system 100 except that system 800 provides an implanted device 802 having a flexible support layer 110 with a magnetic field generator 820 having pillars 832 instead of pillars 132. There are fewer pillars in pillars 832 than pillars 132 and each pillar has a larger aspect ratio (height/diameter). In accordance with one embodiment, each pillar of pillars 832 has a height 860 of 20 micrometers and a diameter of 4 micrometers. Pillars 832 are laid out in a grid pattern with each pillar being separated from its neighbors by a distance 862 of 40 micrometers. Each pillar 832 is substantially higher than the surrounding coil 130.

Figure 9:
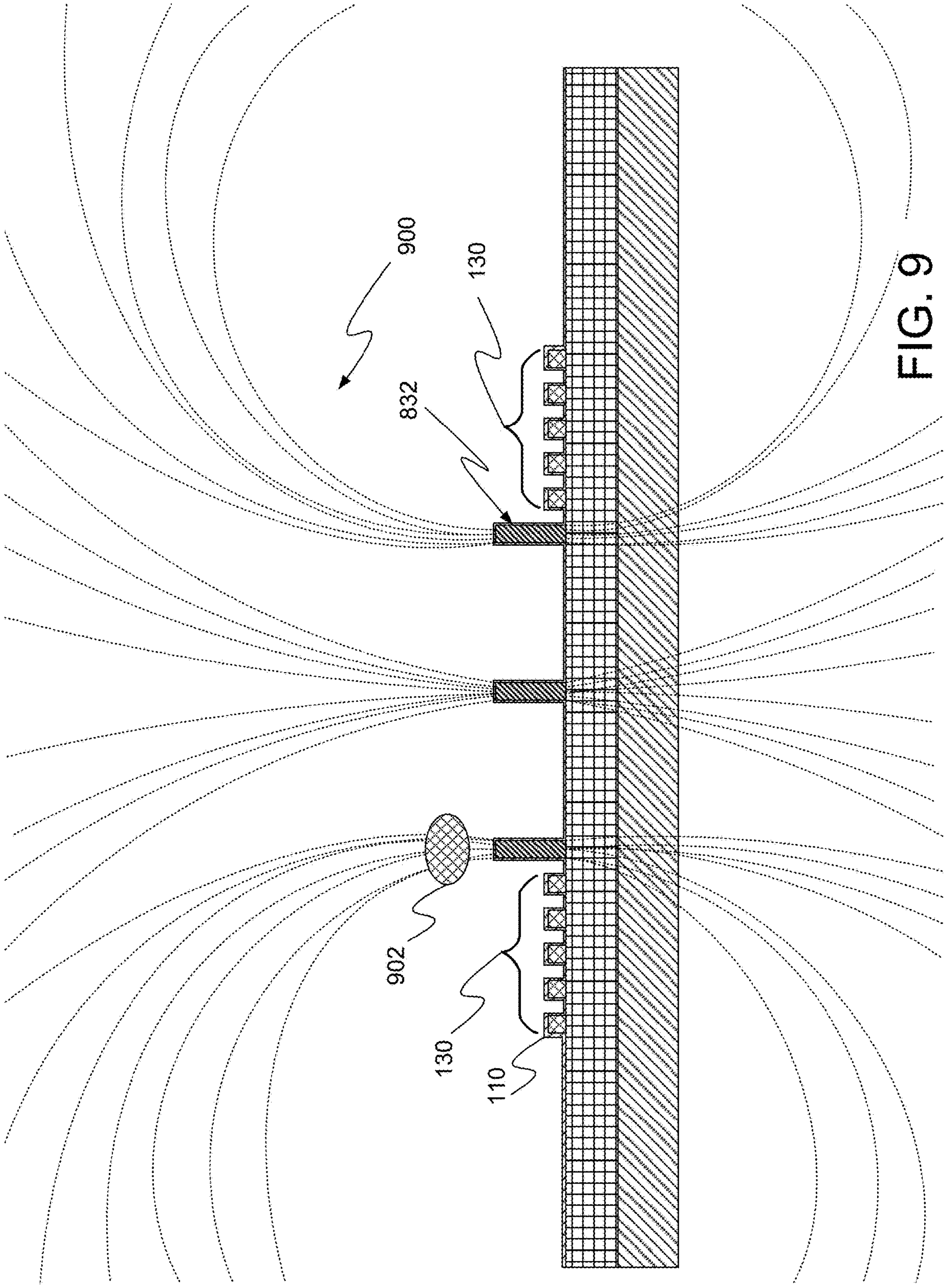
FIG. 9 is a side sectional view of the magnetic field generator of FIG. 8 showing magnetic flux lines.

FIG. 9 shows a side sectional view of magnetic field generator 820 showing magnetic flux lines 900. As shown in FIG. 9, the magnetic flux is concentrated on the pillars 832 and does not pass through the spaces between the pillars. This increases the magnetic flux density above the pillars. The magnetic flux density produced by coil 130 is further amplified by the magnetism of the pillars. This increase in the magnetic flux density makes it more likely that the magnetic field generated by magnetic field generator 820 will affect tissue such as cell 902 shown in FIG. 9.

Figure 10:
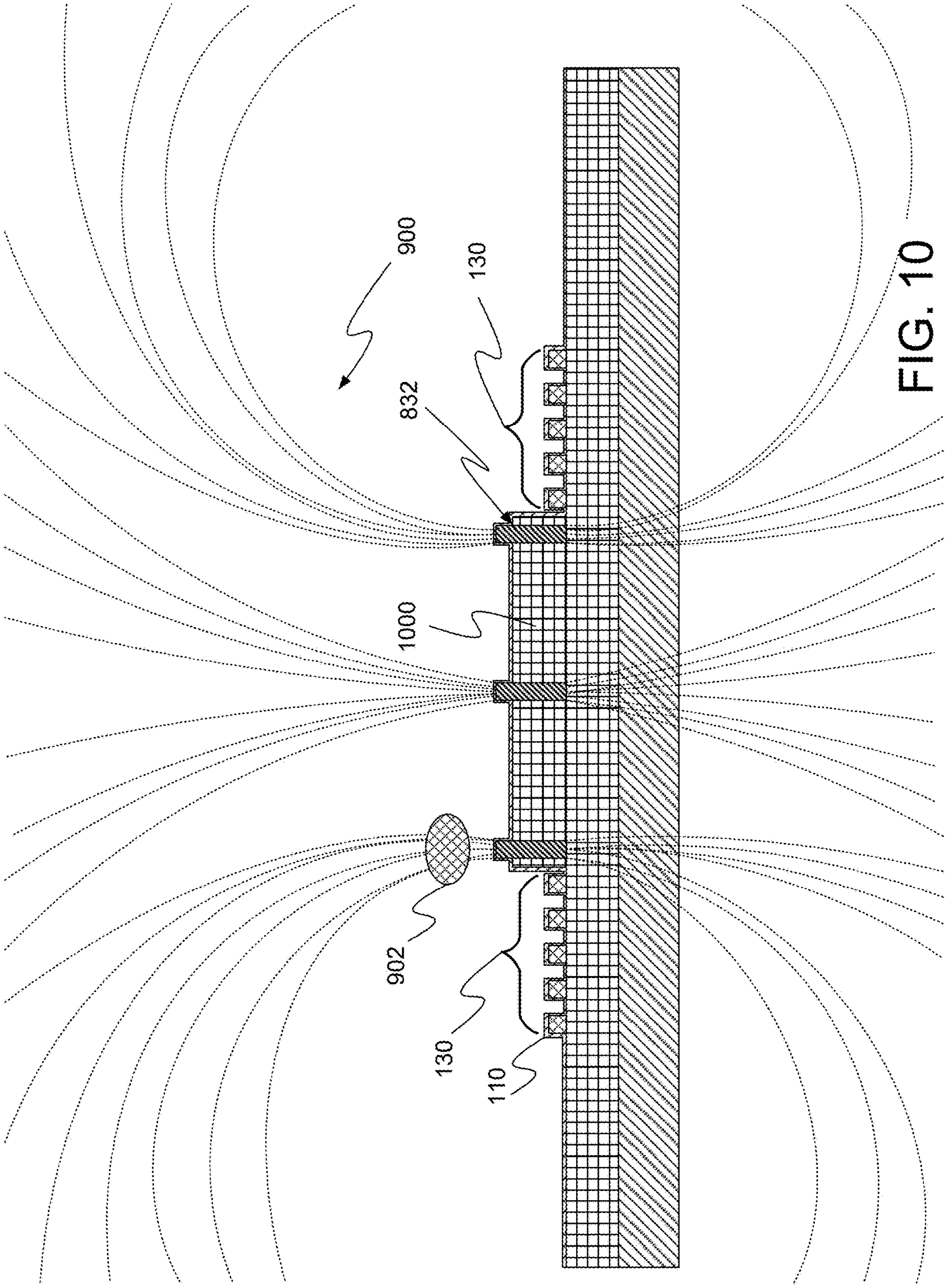
FIG. 10 is a side sectional view of an alternative magnetic field generator of FIG. 8 showing a support structure for the pillars.

FIG. 10 shows a side sectional view of an alternative construction of field generator 820. In FIG. 10, a support material 1000 is deposited around and in contact with pillars 832 to provide mechanical support to pillars 832. Although support material 100 is only shown in FIG. 10, those skilled in the art will recognize that support material can be added to any of the embodiments discussed herein.

Figure 11:
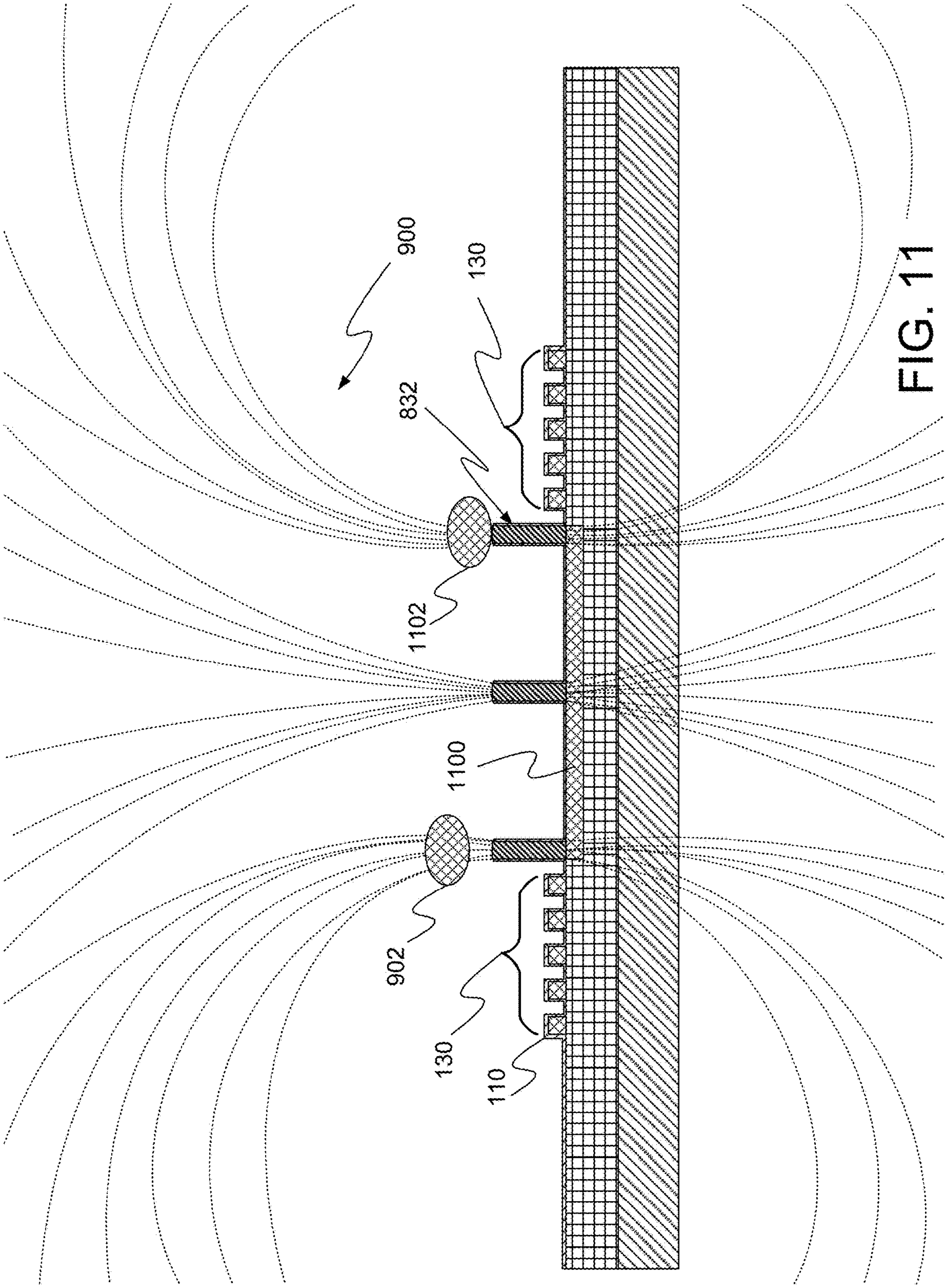
FIG. 11 is a side sectional view of an alternative magnetic field generator of FIG. 8 showing magnetic pillars that also function as electrodes to provide electrical stimulation.

FIG. 11 shows a side sectional view of a further alternative construction of field generator 820 in which pillars 832 are enabled to be used as electrodes. In particular, conductive traces, such as conductive trace 1100, are connected between pillars 832 and stimulator controller 150 and permit stimulator controller 150 to apply an electrical signal to one or more of pillars 832. The tops of pillars 832 are not coated and thus can transfer the electrical signal to surrounding tissue thereby providing electrical stimulation to the tissue, such as cell 1102. In accordance with one embodiment, stimulator controller 150 causes one or more of pillars 832 to provide electrical and magnetic stimulation simultaneously.

Figure 12:
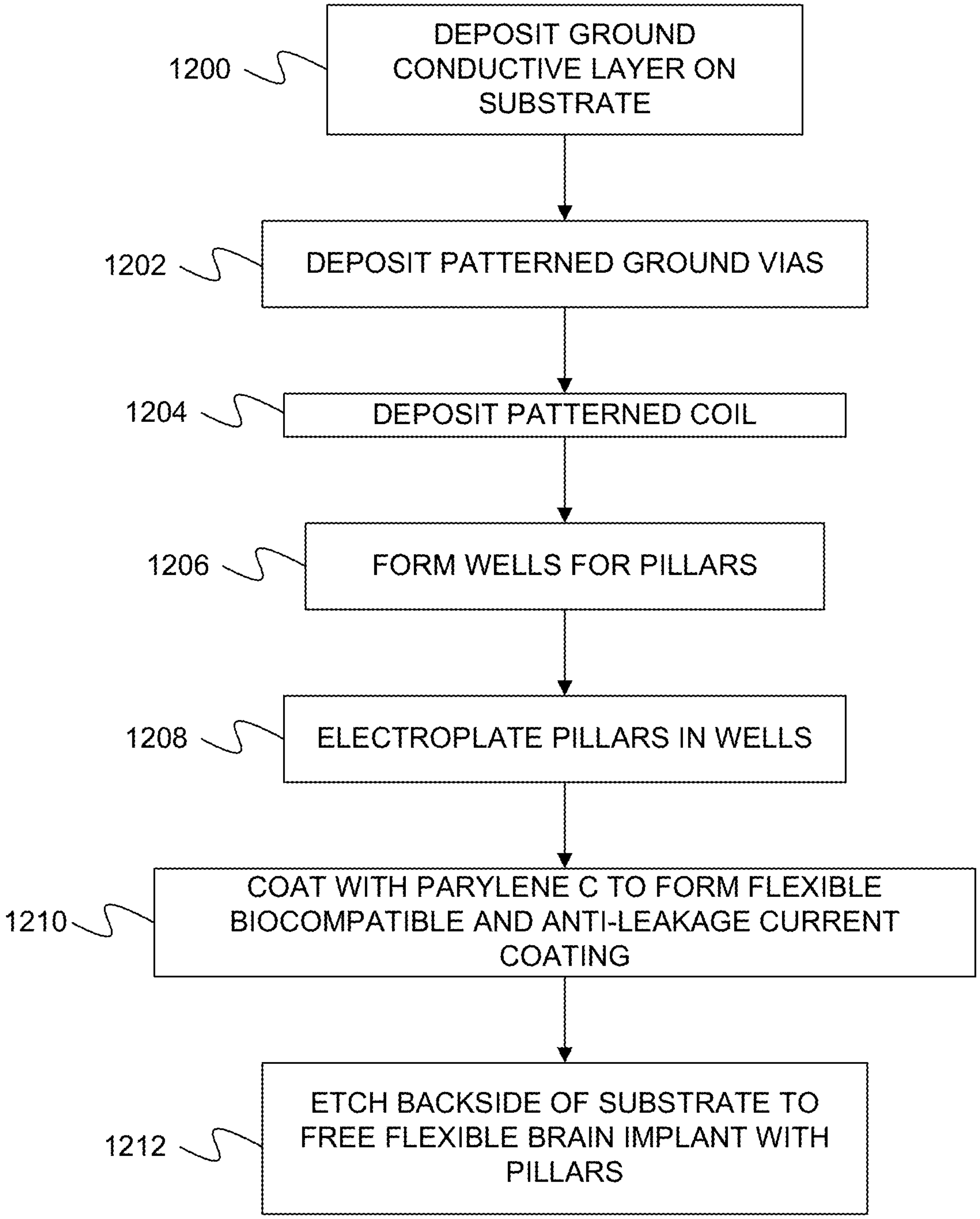
FIG. 12 is a flow diagram of a method of fabricating a stimulator/medical device in accordance with one embodiment.

FIG. 12 provides a method for constructing an implantable structure in accordance with one embodiment. In step 1200, a layer of chromium and a layer of gold are deposited on a silicon substrate to form an electrical ground layer. At step 1202, vias are deposited to connect the ground layer to upper layers at select locations. At step 1204, photoresist is patterned and a layer of chromium and a layer of gold are deposited on the pattern to form an array of coils 130. Photoresist is then patterned to form wells for the pillars at step 1206. Permalloy is electroplated into the wells to form the pillars at step 1208. Parylene C is deposited on the resulting structure at step 1210 to form a biocompatible and anti-leakage current coating that is also a flexible support layer such as support layer 110. While protecting the parylene C layer, the silicon substrate is etched at step 1212 to free the flexible structure including the array of coils 130 on support layer 110.

Figure 13:
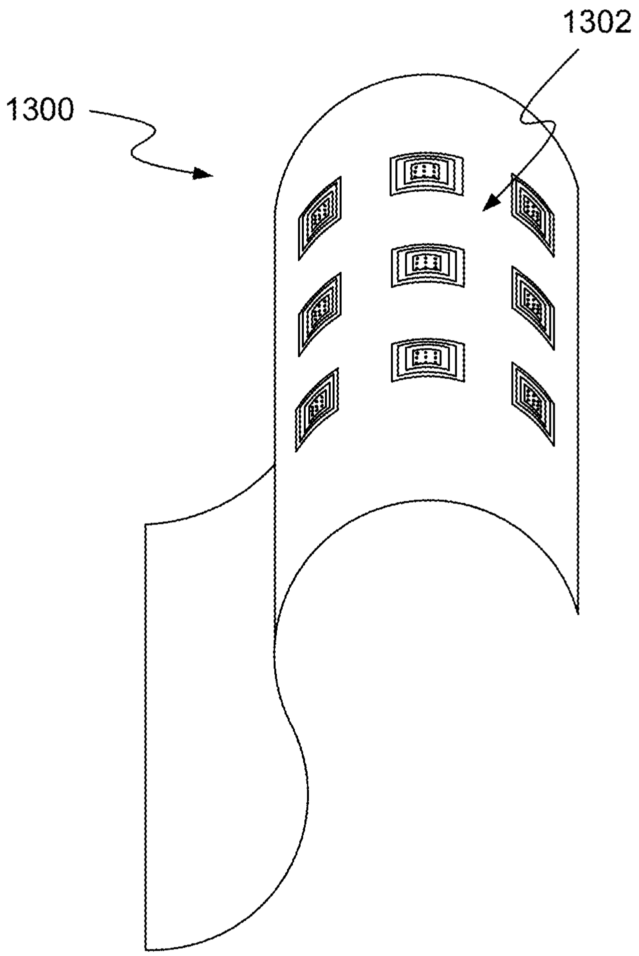
FIG. 13 is a perspective view of a flexible stimulator/medical device in accordance with one embodiment.

FIG. 13 provides a perspective view of a resulting flexible structure 1300 consisting of flexible support layer 110 and an array 1302 of magnetic field generators each consisting of a plurality of pillars surrounded by a respective coil. Flexible structure 1300 can be bent and folded to match the grooves and folds of the brain.

Figure 14:
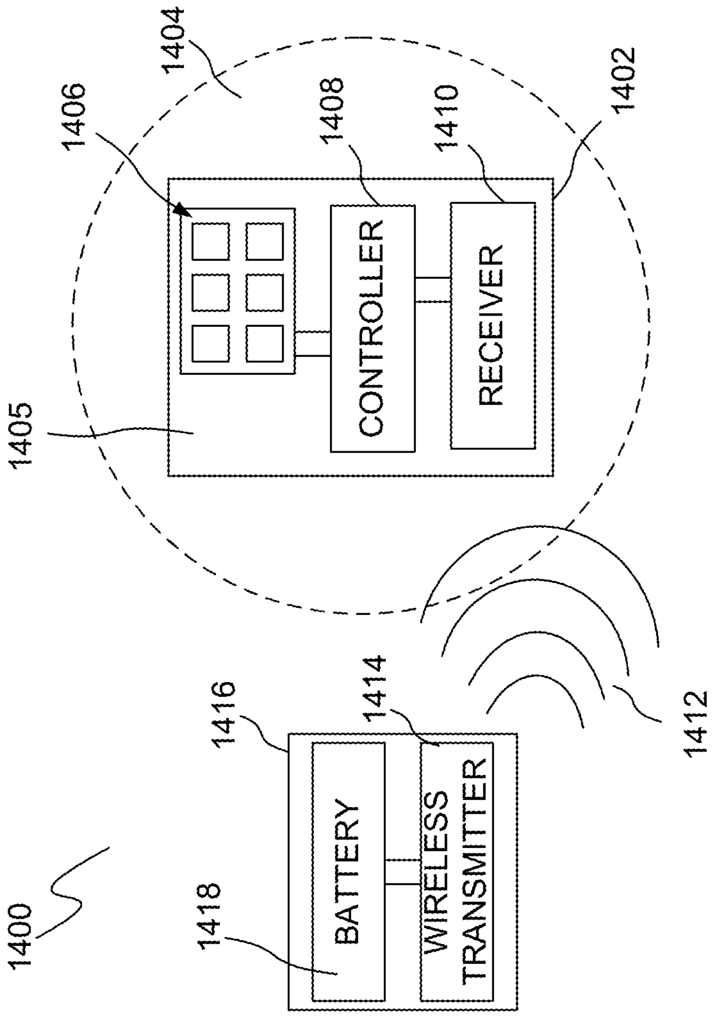
FIG. 14 is a schematic view of a system for providing magnetic field treatments in accordance with a fourth embodiment.

FIG. 14 provides a schematic diagram of an alternative implantable system 1400 that includes an implantable structure 1402 that can be surgically implanted within a living body 1404. Implantable structure 1402 includes an array 1406 of magnetic field generators formed on a flexible support layer 1405. Each magnetic field generator in array 1406 can be any of the magnetic field generators discussed above such as magnetic field generator 120, 620 and 820. Implantable structure 1402 also supports a controller 1408 and a wireless receiver 1410. Controller 1408 controls the application of current to coil 130 of each magnetic field generator in array 1406 to thereby control the magnetic fields generated by the magnetic field generators in array 1406. Wireless receiver 1410 receives a wireless signal 1412 generated by a wireless transmitter 1414 outside of living body 1404. Wireless signal 1412 generates a voltage in receiver 1410 that is then used to provide power to controller 1408. Controller 1408 uses this power to apply the current to magnetic field generators in array 1406. In accordance with one embodiment, wireless transmitter 1414 is contained within a mobile container 1416 that can be carried by the person implanted with structure 1402. Mobile container 1416 also includes a battery 1418, which provides power to wireless transmitter 1414.

While particular numbers of pillars are shown in the exemplary embodiments described above, the number of pillars can range from between two and ten thousand. Further, in accordance with some embodiments, nanowires are used to form the pillars.

Although elements have been shown or described as separate embodiments above, portions of each embodiment may be combined with all or part of other embodiments described above.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms for implementing the claims.

What is claimed is:

1. A stimulator comprising:

a support layer;

a coil supported by the support layer, the coil extending around a central area to form multiple turns around the central area; and a plurality of pillars supported by the support layer in the central area such that each turn of the multiple turns surrounds each pillar of the plurality of pillars.

2. The stimulator of claim 1 wherein the coil comprises gold.

3. The stimulator of claim 1 wherein each pillar of the plurality of pillars comprises a permalloy.

4. The stimulator of claim 1 wherein each pillar and the coil have a same height above the support layer.

5. The stimulator of claim 1 wherein each pillar has a height above the support layer that is greater than a height of the coil above the support layer.

6. The stimulator of claim 1 wherein the plurality of pillars is an array of pillars with rows and columns.

7. The stimulator of claim 1 further comprising an additional plurality of pillars located between turns of the coil.

8. The stimulator of claim 7 wherein the additional plurality of pillars located between turns of the coil have a lower magnetic flux density than the plurality of pillars in the central area.

9. The stimulator of claim 1 further comprising an insulating layer over the coil and the plurality of pillars.

10. The stimulator of claim 1 wherein the plurality of pillars comprises between two pillars and ten-thousand pillars.

11. A method of medical treatment comprising:

placing a magnetic field generator near target tissue, the magnetic field generator comprising:

a conductive coil that wraps around a central volume to form a plurality of turns around the central volume; and a plurality of pillars located within the central volume such that each turn of the plurality of turns surrounds all of the pillars of the plurality of pillars; and applying a series of current pulses to the conductive coil so as to generate a magnetic field that passes through the plurality of pillars and interacts with the target tissue.

12. The method of claim 11 wherein the conductive coil comprises gold.

13. The method of claim 11 wherein each of the plurality of pillars comprises permalloy.

14. The method of claim 11 wherein each of the plurality of pillars has a linear change in a magnetic field generated by the pillar for an applied magnetic field.

15. The method of claim 11 wherein the magnetic field generator further comprises at least one pillar that is not part of the plurality of pillars and is located between turns of the coil.

16. The method of claim 11 wherein the coil and the plurality of pillars are deposited on a substrate.

17. The method of claim 11 wherein the magnetic field interacts with the target tissue to stimulate at least one neuron.

18. The method of claim 11 wherein the magnetic field interacts with the target tissue to destroy the target tissue.

19. A medical treatment device comprising:

a plurality of magnetic pillars;

a coil wrapping around the plurality of magnetic pillars, the coil comprising a plurality of turns such that each turn surrounds all of the magnetic pillars of the plurality of magnetic pillars; and a controller configured to apply a current to the coil to generate a magnetic field that passes through the plurality of magnetic pillars.

20. The medical treatment device of claim 19 wherein at least one of the plurality of magnetic pillars functions as an electrode to enable both magnetic and electric stimulation simultaneously.

21. A stimulator comprising:

a support layer;

a coil supported by the support layer, the coil extending around a central area; and a plurality of pillars supported by the support layer in the central area;

wherein each pillar and the coil have a same height above the support layer.

22. A method of medical treatment comprising:

placing a magnetic field generator near target tissue, the magnetic field generator comprising:

a conductive coil that wraps around a central volume; and a plurality of pillars located within the central volume; and applying a series of current pulses to the conductive coil so as to generate a magnetic field that passes through the plurality of pillars and interacts with the target tissue to destroy the target tissue.

23. A medical treatment device comprising:

a plurality of magnetic pillars;

a coil wrapping around the plurality of magnetic pillars; and a controller configured to apply a current to the coil to generate a magnetic field that passes through the plurality of magnetic pillars;

wherein at least one of the plurality of magnetic pillars functions as an electrode to enable both magnetic and electric stimulation simultaneously.

* * * * *